(12) United States Patent
Yamasaki et al.

(10) Patent No.: US 6,576,446 B2
(45) Date of Patent: Jun. 10, 2003

(54) PROCESS FOR PRODUCING HIGH 2-O-α-D-GLUCOPYRANOSYL-L-ASCORBIC ACID

(75) Inventors: Hiroshi Yamasaki, Okayama (JP); Koichi Nishi, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/875,963

(22) Filed: Jun. 8, 2001

(65) Prior Publication Data

US 2001/0051711 A1 Dec. 13, 2001

(30) Foreign Application Priority Data

Jun. 8, 2000 (JP) ........................................ 2000-172643

(51) Int. Cl.⁷ ................................. C12P 19/44
(52) U.S. Cl. .......................... 435/74; 435/75; 435/136; 435/146; 536/4.1; 536/127
(58) Field of Search .............................. 435/74, 75, 136, 435/146; 536/4.1, 127

(56) References Cited

U.S. PATENT DOCUMENTS 5,508,391 A 4/1996 Sakai et al.

FOREIGN PATENT DOCUMENTS

| EP | 0 425 066 | 3/1990 |
| JP | 183492/91 | 8/1991 |
| JP | 6 228183 | 8/1994 |

OTHER PUBLICATIONS

Scopes, Protein Purification, Principles and Practice, Spring–Verlag, New York, pp. 113–126, 1987.*

* cited by examiner

*Primary Examiner*—Francisco Prats
(74) *Attorney, Agent, or Firm*—Browdy and Neimark PLLC (57) ABSTRACT

Disclosed is a process for producing a high αG-AA content product, which comprises the steps of: contacting a solution as a material solution, containing αG-AA, L-ascorbic acid, and a saccharide(s), with an anion exchange resin packed in a column to adsorb the αG-AA and L-ascorbic acid on the anion exchanger; washing the anion exchanger with water to remove the saccharide(s) therefrom; feeding to the column an aqueous solution, as an eluent, of an acid and/or a salt with a concentration of less than 0.5 N to fractionate a fraction rich in 2-O-α-D-glucopyranosyl-L-ascorbic acid and a fraction rich in L-ascorbic acid; and collecting the former fraction.

9 Claims, 4 Drawing Sheets

Conventional process

Reaction

↓

Filtration

↓

Demineralization

↓

Column chromatography using anion exchange resin

↓

Concentration

↓

Column chromatography using strong-acid exchange resin

↓

Concentration

↓

Product

FIG. 1

The present process

Reaction
↓
Filtration
↓
Demineralization
↓
Column chromatography using anion exchange resin
↓
Concentration
↓
Product

PROCESS FOR PRODUCING HIGH 2-O-α-D-GLUCOPYRANOSYL-L-ASCORBIC ACID

BACKGROUND OF THE INVENTION

1. Field of the Invention

The present invention relates to a novel process for producing a high-content product of 2-O-α-D-glucopyranosyl-L-ascorbic acid (hereinafter abbreviated as "αG-AA", unless specified otherwise), a stabilized L-ascorbic acid.

2. Description of the Prior Art

As disclosed in Japanese Patent Kokai No. 183,492/91, αG-AA is known to have the following satisfactory physicochemical properties:

(1) It is not directly reducible, but has outstandingly high stability, and, unlike L-ascorbic acid, it does not cause a Maillard reaction and unnecessary reaction even when in the presence of amino acids, peptides, proteins, lipids, saccharides, or physiologically active substances, but it stabilizes them;

(2) Upon hydrolysis, it forms L-ascorbic acid, then exhibits substantially the same reducing and anti-oxidation actions as L-ascorbic acid;

(3) It is easily hydrolyzed by in vivo enzymes into L-ascorbic acid and D-glucose to exhibit the physiological activities inherent to L-ascorbic acid, and is capable of enhancing the physiological properties of vitamins E and P when used in combination;

(4) It is highly safe because it is naturally formed in a slight amount though and, when orally taken, it is metabolized in vivo into L-ascorbic acid and a substance such as an α-glucosyl saccharide compound;

(5) Although αG-AA in a crystalline form is non- or substantially non-hygroscopic, it has a relatively-high solubility rate and solubility in water, and thus it can be advantageously used as a vitamin C-enriching agent, taste improver, acid-imparting agent, or stabilizer for vitamin preparations in the form of a powder, granule or tablet; and used in foods and beverages such as sand creams, chocolates, chewing gums, instant juices, and instant seasonings; and (6) It has satisfactory handleability because αG-AA in a crystalline form is non- or substantially non-hygroscopic and keeps its free-flowing ability without solidification during storage. As compared with αG-AA in a non-crystalline form, αG-AA in a crystal form can highly cut physical and labor costs required in its package, transportation, and storage.

αG-AA is now widely used in a cosmetic field mainly and is expected for its explorative use in other various fields such as food products, pharmaceuticals, feeds, pet foods, and industrial materials.

Figure 1:
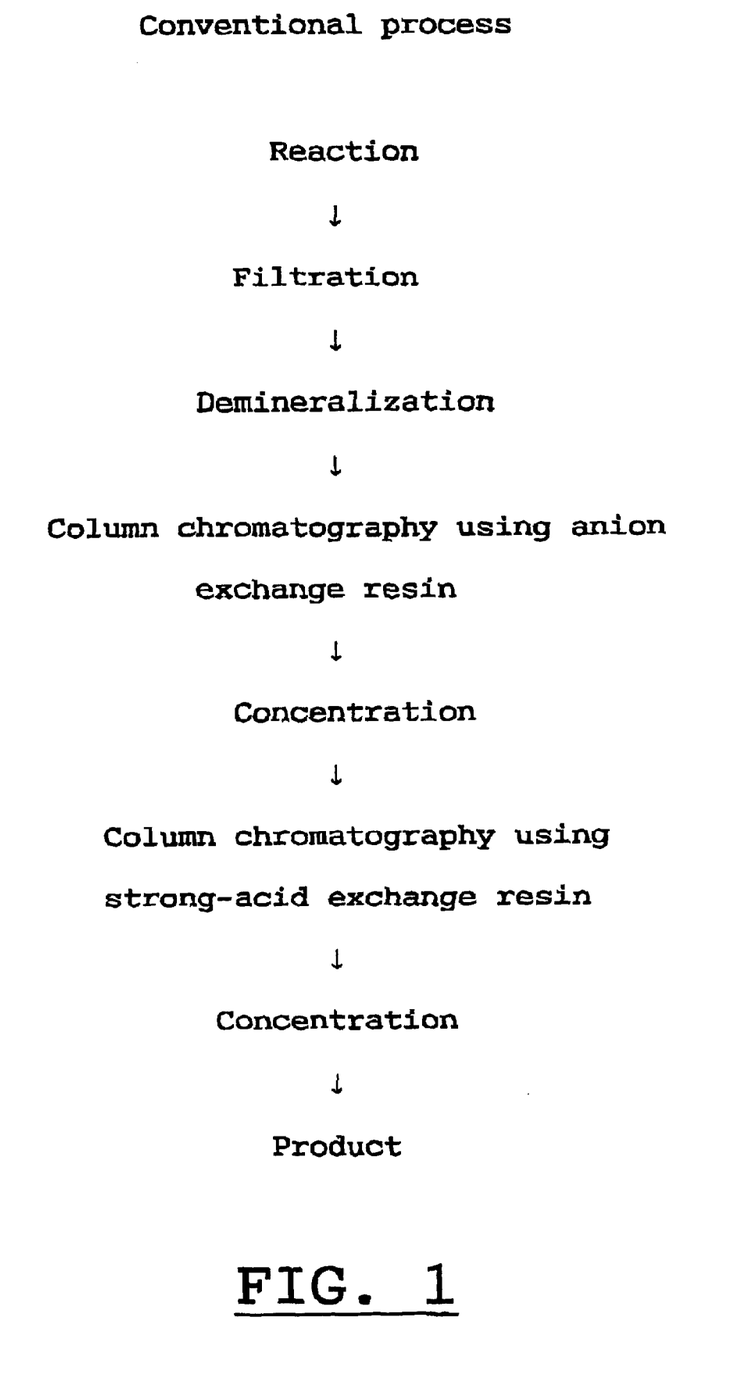
FIG. 1 is a flow chart of a conventional process for producing a high αG-AA content product.

As a representative example of industrial process for producing αG-AA is, for example, a process as disclosed in Japanese Patent Kokai No. 183,492/91. The process, as shown in FIG. 1, comprises the steps of contacting a solution containing L-ascorbic acid and an α-glucosyl saccharide compound(s) with a saccharide-transferring enzyme or glucoamylase (EC 3.2.1.3) to form αG-AA to obtain a solution comprising αG-AA, intact L-ascorbic acid, α-glucosyl saccharide compound(s) and other saccharides produced from the α-glucosyl saccharide compound(s) filtering the resulting solution; removing minerals from the filtrate by subjecting the filtrate to column chromatography using a cation-exchange resin (H-form); subjecting the demineralized solution to column chromatography using an anion-exchange resin to adsorb αG-AA and L-ascorbic acid on the anion-exchange resin; washing the anion-exchange resin with water to remove saccharides from the column; eluting the αG-AA and the L-ascorbic acid from the anion-exchange resin; concentrating the eluate; subjecting the concentrate to column chromatography using a strong-acid cation exchange resin to fractionate into a fraction rich in αG-AA and a fraction rich in L-ascorbic acid; and concentrating the former fraction into a high αG-AA content product.

In the above column chromatography using an anion-exchange resin, αG-AA and L-ascorbic acid are simultaneously desorbed from the resin, and this yields αG-AA in a mixture form with L-ascorbic acid. To obtain a high αG-AA content product, solutions containing αG-AA and L-ascorbic acid should inevitably be first concentrated, then fractionated into a fraction rich in αG-AA and a fraction rich in L-ascorbic acid As described above, in conventional process for producing high αG-AA content product, two steps of column chromatography using an anion-exchange resin and a cation-exchange resin are inevitably required, and the eluate from the column chromatography using the anion-exchange resin should be first concentrated before fed to column chromatography using the cation-exchange resin, and, as the demerits, these complicate the preparation of αG-AA, lower the yield of high αG-AA content products, and increase the production cost.

Under these circumstances, there has been in a great demand an industrial-scale production of high αG-AA content products with relatively-high quality and satisfactory processibility, production cost, and yield.

SUMMARY OF THE INVENTION

The object of the present invention is to provide an industrial-scale production of high αG-AA content products with relatively-high quality and satisfactory processibility, production cost, and yield. The term "high αG-AA content product(s)" as referred to in the present invention means high αG-AA content product(s) which contain(s) at least 80% (w/w) of αG-AA ("% (w/w)" may be abbreviated as "%", hereinafter) on a dry solid basis (d.s.b.), preferably, at least 90%, and which may have any form of a liquid, paste, solid or powder.

In view of the foregoing, the present inventors continued studies on a simpler process for producing high αG-AA content products by contacting a solution containing αG-AA and L-ascorbic acid with an ion-exchange resin packed in a column. As a result, they found that the object can be attained by using an anion-exchange resin as an ion-exchange resin to be packed in a column; allowing αG-AA and L-ascorbic acid to adsorb on the anion resin; feeding to the column an aqueous solution, as an eluent, of an acid and/or a salt with a concentration of less than 0.5 N to fractionate into a fraction rich in αG-AA and a fraction rich in L-ascorbic acid; and collecting the former fraction.

Figure 2:
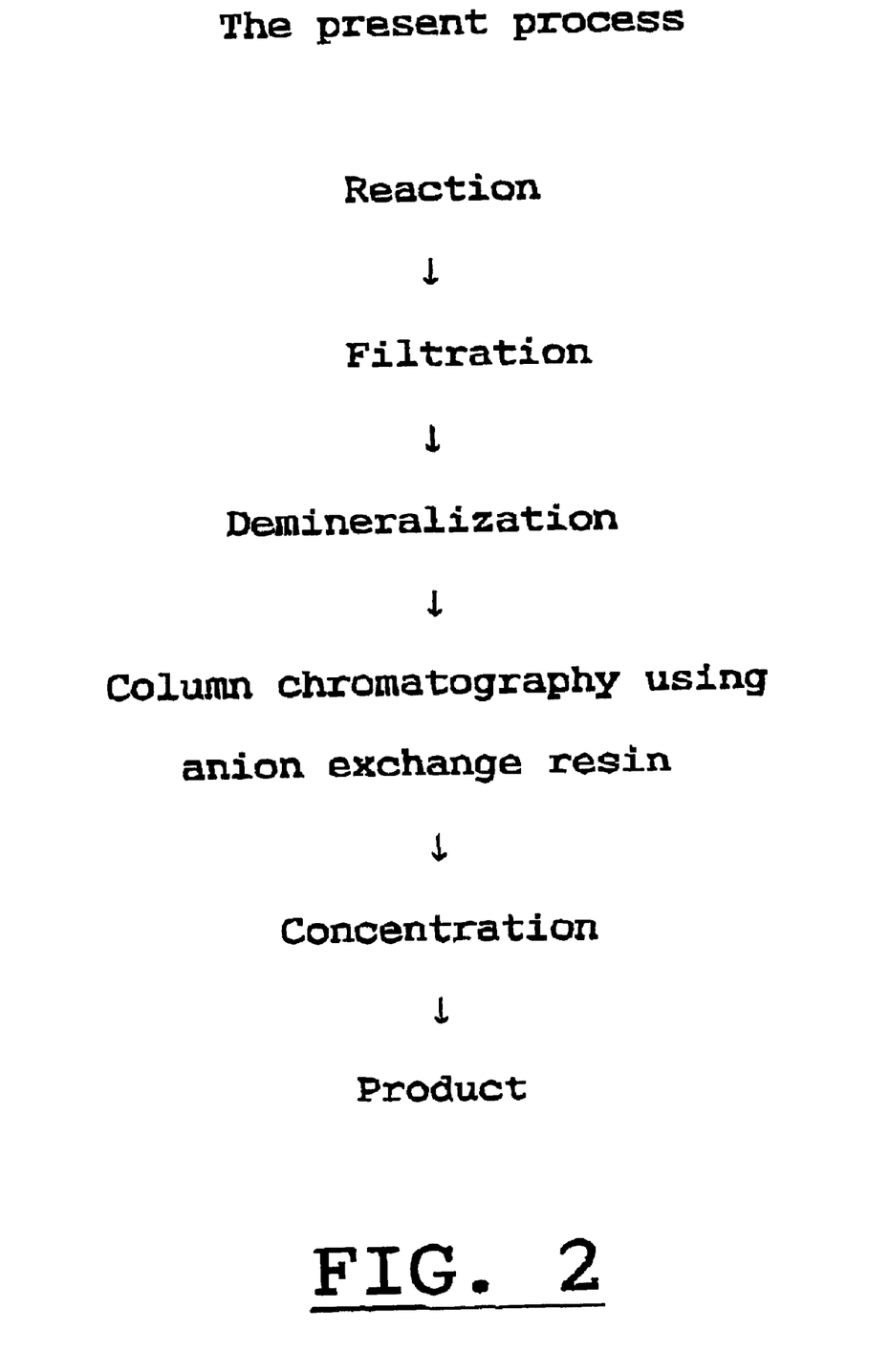
FIG. 2 is a flow chart of the present process for producing a high αG-AA content product.

As shown in FIG. 2, the process for producing high αG-AA content product according to the present invention is characterized in that it comprises the steps of allowing a saccharide-transferring enzyme with or without glucoamylase to act on a solution containing L-ascorbic acid and an α-glucosyl saccharide compound(s) to obtain a solution containing αG-AA, L-ascorbic acid, and saccharides; filtering the solution; demineralizing the filtrate; contacting the demineralized solution, as a material solution, with an anion-exchange resin packed in a column to adsorb on the resin αG-AA and L-ascorbic acid; washing the resin with water to remove saccharides from the column; feeding an aqueous solution of an acid and/or a salt with a concentration of less than 0.5 N to fractionate a fraction rich in αG-AA and a fraction rich in L-ascorbic acid; and concentrating the former fraction to obtain a high αG-AA content product. According to the present invention, αG-AA, and L-ascorbic acid can be separated by column chromatography using an anion-exchange resin, resulting in a cancellation of the column chromatography using a strong-acid cation exchange resin which is inevitably used in a conventional preparation as shown in FIG. 1. As a result, relatively-high quality products rich in αG-AA with advantageous processibility, economical viewpoint, and yield can be produced in an industrial scale.

EXPLANATION OF SYMBOLS

The symbols "-○-", "-●-", and "-Δ-" mean "αG-AA", "L-ascorbic acid", and "saccharides", respectively.

DETAILED DESCRIPTION OF THE INVENTION

Explaining the solutions used in the present invention, they are aqueous solutions which contain αG-AA, L-ascorbic ascorbic acid, and a saccharide(s). The process for producing the solutions should not be restricted to specific ones, independently of enzymatic or synthetic methods, as long as they provide solutions containing αG-AA, L-ascorbic acid, and a saccharide(s). As a preventative example of such a process, one comprising a step of allowing a saccharidetransferring enzyme with or without glucoamylase to act on a solution containing L-ascorbic acid and an α-glucosyl saccharide compound(s), e.g., the process disclosed in Japanese Patent Kokai No. 183,492/91.

The solutions preferably used in the present invention have a solid concentration, usually, of 1–75% (w/v), preferably, 10–70% (w/v), more preferably, 20–60% (w/v), and most preferably, 30–40% (w/v). Since Lascorbic acid is susceptible to decomposition under alkaline conditions, the solutions should preferably be set to acid pHs, usually, pHs less than 7, preferably, pHs of 1.0–6.5, more preferably, pHs of 1.5–6.0. Prior to contacting the solutions with anion-exchange resins, impurities such as anions, organic acids, and amino acids that are coexisted in the solutions should be removed or lowered as much as possible because of the use of anionexchange resins (OH-form)

The term "α-glucosyl saccharide compound(s)" as referred to in the present invention means those which can form α-glycosyl-L-ascorbic acid including αG-AA and which are composed of equimolar or more α-D-glucosyl residues bound to L-ascorbic acid via the action of a saccharidetransferring enzyme. Examples of such α-glucosyl saccharide compounds are maltooligosaccharides such as maltose, maltotriose, maltotetraose, maltopentaose, maitohexaose, maltoheptaose, and maltooctaose; partial starch hydrolysates such as dextrins, cyclodextrins, and amyloses; and others such as liquefied starches, gelatinized starches, and soluble starches. To facilitate the formation of αG-AA, preferably α-glucosyl saccharide compounds suitable for the saccharide-transferring enzyme are preferably used. For example, when α-glucosidase (EC 3.2.1.20) is used as a saccharidetransferring enzyme, maltooligosaccharides such as maltose, maltotriose, maltotetraose, maltopentaose, maltohexaose, maltoheptaose, and maitooctaose; dextrins with a DE (dextrose equivalent) of about 50–60, and partial starch hydrolysates can be preferably used as α-glucosyl saccharide compounds. When cyclomaltodextrin glucanotransferase (EC 2.4.1.19) is used as a saccharidetransferring enzyme, cyclodextrins and partial starch hydrolysates such as gelatinized starches and dextrins with a DE from less than one to about 60 are preferably used. In the case of using α-amylase (EC 3.2.1.1) as a saccharide-transferring transferring enzyme, partial starch hydrolysates such as gelatinized starches and dextrins with a DE from less than one to about 30 are preferably used.

The concentration (% (w/v)) of L-ascorbic acid used in the above saccharide-transferring enzymatic reaction is usually at least 1% (w/v), preferably, about 2-30% (w/v), while the preferable concentration of an α-glucosyl saccharide compound is usually about 0.5-30 folds of that of the L-ascorbic acid used.

Independently of their properties, features and origins, any saccharidetransferring enzymes can be used in the present invention as long as they form α-glycosyl-L-ascorbic acid such as αG-AA in which at least one α-glucosyl residue is transferred to the alcohol group at C-2 of L-ascorbic acid without decomposing L-ascorbic acid when allowed to act on an aqueous solution containing Lascorbic acid and an α-glucosyl saccharide compound(s). For example, the α-glucosidases usable as the saccharide-transferring enzyme in the present invention include those which are of animal origin such as those from murine renes, rat intestinal mucosas, and small intestines of dogs and pigs; plant origin such as those from rice seeds and corn seeds; and bacterial origin such as those from fungi of the genera Mucor and Penicillium and yeasts of the genus Saccharomyces. Examples of other saccharide-transferring enzymes, i.e., cyclomaltodextrin glucanotransferas includes those which are obtain from the genera Bacillus and Klebsiella, while examples of other saccharide-transferring enzymes, i.e., α-amylases are obtained from the genus Bacillus.

These saccharide-transferring enzymes should not necessarily be in a purified form, and those in a crude form can be also used in the present invention. However, such crude enzymes can be preferably purified by conventional methods prior to use. In the present invention, commercialized saccharide-transferring enzymes can be used. In use, the above enzymes can be arbitrarily used in an immobilized form. Any pHs and temperatures for the saccharide-transferring enzymatic reaction can be used in the present invention as long as the saccharide-transferring enzymes act on L-ascorbic acid and α-glucosyl saccharide compounds to form αG-AA: Usually, it is selected from pus of 3–9, preferably, pHs of 4–7, and temperatures of about 20° C. to about 80° C. Since the amount of the enzymes used and the enzymatic reaction time are closely related each other, the amount of enzyme is usually chosen from the above range so as to complete the enzymatic reaction within about 3–80 hours from an economical viewpoint. When used in an immobilized form, the saccharide-transferring enzymes can be advantageously used in a batch-wise or in a continuous manner.

During the enzymatic reaction, L-ascorbic acid is susceptible to decomposition by the oxygen present in the reaction system; it should preferably be kept in reduced oxygen or non-oxygen conditions or reducing conditions, and if necessary, thiourea and sulfites can be preferably added. Because L-ascorbic acid is susceptible to decomposition by light, it should preferably be reacted under dark- or light shielded-conditions.

If necessary, α-glycosyl-L-ascorbic acid containing αG-AA can be formed by mixing microorganisms with saccharide-transferring ability in growth media with L-ascorbic acid and α-glucosyl saccharide compounds.

The α-glycosyl-L-ascorbic acid formed via the action of a saccharide-transferring enzyme is a compound composed of one or more α-D-glucosyl residues bound to the alcohol group at C-2 of L-ascorbic acid. The number of α-D-glucosyl residues, that are bound via the α-1,4 linkage, is usually about two to seven. Examples of such α-glycosyl-L-ascorbic acid are αG-AA, 2-O-α-D-maltosyl-L-ascorbic acid, 2-O-α-D-maltotriosyl-L-ascorbic acid, 2-O-α-D-maltotetraosyl-L-ascorbic acid, 2-O-α-D-maltopentaosyl-L-ascorbic acid, 2-O-α-D-maltohexaosyl-L-ascorbic acid, and 2-O-α-D-maltoheptaosyl-L-ascorbic acid. When α-glycosyl-L-ascorbic acid is formed by using α-glucosidase, only αG-AA is usually formed. Depending on the saccharide-transferring enzymes and the reaction conditions used, α-glycosyl-L-ascorbic acids such as 2-O-α-D-maltosyl-L-ascarbic acid and 2-O-α-D-maltotriosyl-L-ascorbic acid are formed together with αG-AA.

In the case of forming α-glycosyl-L-ascorbic acids using cyclomaltodextrin glucanotransferase or α-amylase, α-glycosyl-L-ascorbic acids, which have more α-D-glucosyl residues than those produced with α-glucosidase, can be usually formed together with αG-AA. In general, when cyclomaltodextrin glucanotransferase is used, α-glycosyl-L-ascorbic acids composed of about one to seven α-D-glucosyl residues bound to L-ascorbic acid are formed, while in the case of using α-amylase, lesser types of α-glycosyl-L-ascorbic acids tend to form.

Combination use of a saccharide-transferring enzyme and glucoamylase to form αG-AA can increase the yield of αG-AA. In general, to increase the saccharide-transferring reaction efficiency, saccharide-transferring enzyme is preferably first allowed to act on L-ascorbic acid and an α-glucosyl saccharide compound(s) to transfer equimolar or more α-D-glucosyl residues to L-ascorbic acid and to form a mixture of α-glycosyl-L-ascorbic acids and αG-AA, and then allowing glucoamylase to act on the resulting mixture to hydrolyze α-D-glucosyl residues, that are bound to the α-glycosyl-L-ascorbic acids other than αG-AA, and to form and accumulate αG-AA.

The glucoamylase used in the present invention includes those which are from microorganism, plant, and animal origins Usually, commercialized glucoamylases from bacteria of the genera Aspergillus and Rhizopus can be advantageously used. In this case, β-amylase (EC 3.2.1.2) can be arbitrarily used along with such glucoamylases.

Explaining the anion-exchange resins used in the present invention, any one of those in the form of a gel, macro-reticular (MR-form), or macroporous structure as a mother structure can be used, and any one of strong- or weak-base styrene (styrene-divinylbenzene copolymer) and acrylic anion-exchange resins can be used as a basal material. Any anion-exchange resins in a strong-alkaline (I and II types), neutral, or week-alkaline form can be used in the present invention as long as they have anion-absorbing ability. Examples of such anion exchangers now commercially available are "AMBERLITE IRA67", "AMBERLITE IRA96SB", "AMBERLITE IRA400", "AMBERLITE IRA401B", "AMBERLITE IRA402", "AMBERLITE IRA402BL", "AMBERLITE IRA410", "AMBERLITE IRA411S", "AMBERLITE IRA440B", "AMBERLITE IRA458RF", "AMBERLITE IRA473", "AMBERLITE IRA478P", "AMBERLITE TPA900", "AMBERLITE IRA904", "AMBERLITE IRA910CT", "AMBERLITE IRA958", "AMBERLITE XT5007", "AMBERLITE XT6050RF", "AMBERLITE XE583", and "AMBERLITE CG400", which are all commercialized by Rohm & Haas Co., Pennsylvania, U.S.A.; and "DIAION SA10A", "DIAION SA11A", "DIAION SA12A", "DIAION SA20A", "DIAION SA21A", "DIAION NSA100", "DIAION PA308", "DIAION PA312", "DIAION PA316", "DIAION PA408", "DIAION PA412", "DIAION PA418", "DIAION HPA25", "DIAION HPA75", "DIAION WA10", "DIAION WA20", "DIAION WA21J", "DIAION WA30", and "DIAION DCA11", which are all commercialized by Mitsubishi Chemical Industries, Ltd., Tokyo, Japan; "DOWEX SBR", "DOWEX SBR-P-C", "DOWEX SAR", "DOWEX MSA-1", "DOWEX MSA-2", "DOWEX MSA-22", "DOWEX MSA-66", "DOWEX MWA-1", "DOWEX MONOSPHERE 550A", "DOWEX MAASON A", "DOWEX MARASON A2", "DOWEX 1X2", "DOWEX 1X4", "DOWEX 1X8", and "DOWEX 2X8" which are all commercialized by The Dow Chemical Co., Michigan, U.S.A. Among these anion exchangers, "AMBERLITE IPA411S", "DIAION WA30", "AMBERLITE IRA478RF", and "AMBERLITE IRA 910CT" can be preferably used in the present invention because of their relatively high absorbability and separability of αG-AA and L-ascorbic acid. As for the ion forms of the anion exchange resins, those in the form of OH, Cl and $CH_3COO$ can be appropriately used in the present invention, those in the form of OH can be advantageously used in view of their absorbability.

The eluents used in the present invention include one or more acids such as hydrochloric acid, sulfuric acid, nitric acid, and citric acid, as well as aqueous solutions thereof; and one or more salts such as sodium chloride, potassium chloride, sodium sulfate, sodium nitrate, potassium nitrate, sodium citrate, and potassium citrate, as well as aqueous solutions thereof. One or more of the above acids and salts can be used in an appropriate combination. When used aqueous salt solutions as eluents, αG-AA contained in eluates, which had been desorbed and eluted from columns packed with anion exchangers, is generally in a salt form. If necessary, such αG-AA can be demineralized and converted into a free acid form of cxG-AA by using cation exchangers (H-form). When used aqueous acid solutions as eluents, αG-AA contained in eluates, which had been desorbed and eluted from columns packed with anion exchangers, is generally in a free acid form. Among the aqueous acid solutions used as eluents in the present invention, aqueous solutions of hydrochloric acid can be advantageously used for economy and ease of regeneration of anion exchange resins. The concentration of aqueous solutions of acids or salts used as eluents should not necessarily be set to a constant level, and if necessary, it can be changed stepwisely or linearly as in a gradient elution manner. The eluents once used in desorbing and eluting αG-AA and L-ascorbic acid can be recovered and reused to lower the production costs.

The method for producing high αG-AA content products using the aforesaid material solutions, anion exchange resins, and eluates are as follows: As described above, the material solutions used in the present invention usually contain αG-AA, L-ascorbic acid, and α-glucosyl saccharide compounds, as well as α-glucosyl saccharide compounds, D-glucose from the α-glucosyl saccharide compounds, saccharides such as hydrolyzates of the α-glucosyl saccharide compounds, and salts. Thus, the material solutions are first filtered, then demineralized using cation exchange resins (H-form) with or without activated carbons. The demineralized solutions are contacted with anion exchange resins packed in columns to absorb thereupon αG-AA and L-ascorbic acid, followed by washing the columns with water to remove saccharides, feeding to the columns aqueous solutions of acids and/or salts with a concentration of less than 0.5 N as eluents to fractionate into a fraction rich in αG-AA and a fraction rich in L-ascorbic acid, and collecting the former fraction. In this case, the separated intact L-ascorbic acid and α-glucosyl saccharide compounds can be reused as materials for the next saccharide-transferring reaction from an economical viewpoint.

The column used in the present invention can be constructed by one or more columns, having an appropriate shape, size, and length, cascaded in series or connected in parallel. When plural columns are used, they can be cascaded in series to give an appropriate column bed-depth. The flow rate for feeding the material solutions to anion exchange resins is preferably SV (space velocity) b 5or lower, more preferably, SV 1–3. The flow rate for feeding eluents to anion exchange resins is preferably SV 1 or lower, more preferably, SV 0.3–0.7. The order of a fraction rich in αG-AA and a fraction rich in L-ascorbic acid eluted from columns can be changed by altering the types of anion exchange resins used, particularly, by varying the mother structures and functional groups of the anion exchange resins. The temperatures during column chromatography are usually those in the range of 0–80° C., preferably, 10–40° C., and more preferably, 15–25° C., by taking into consideration the influence of temperature on the decomposition of αG-AA and L-ascorbic acid. When used aqueous solutions of acids and/or salts with concentrations of at least 0.5 N, αG-AA is promptly and easily desorbed from anion exchange resins and eluted from columns, while L-ascorbic acid is also desorbed and eluted together with αG-AA, resulting in their insufficient separation and in a difficulty of obtaining fractions rich in αG-AA with a relatively-high purity and yield. In the case of using, as eluents, aqueous solutions of acids and/or salts with a total concentration of less than 0.5 N, preferably, 0.1–0.45 N, and more preferably 0.2–0.3 N, αG-AA and L-ascorbic acid are respectively desorbed and eluted from anion exchange resins packed in columns as their respective enriched fractions, resulting in an efficient separation and collection of their enriched fractions in a satisfactorily-high yield. In such a column chromatography, fractions rich in αG-AA and fractions rich in L-ascorbic acid can be obtained even with aqueous solutions of acids and/or salts with concentrations of less than 0.1 N, however, the desorption and elution time required for αG-AA and L-ascorbic acid from anion exchange resins tends to be longer and the concentration of the resulting αG-AA tends to be lower. L-ascorbic acid is also desorbed and eluted together with αG-AA, resulting in their insufficient separation and in a difficulty of obtaining fractions rich in αG-AA with a relatively-high purity and yield. In the case of using, as eluents, aqueous solutions of acids and/or salts with a total concentration of less than 0.5 N, preferably, 0.1–0.45 N, and more preferably 0.2–0.3 N, αG-AA and L-ascorbic acid are respectively desorbed and eluted from anion exchange resins packed in columns as their respective enriched fractions, resulting in an efficient separation and collection of their enriched fractions in a satisfactorily-high yield. In such a column chromatography, fractions rich in αG-AA and fractions rich in L-ascorbic acid can be yielded even with aqueous solutions of acids and/or salts with concentrations of less than 0.1 N, however, the desorption and elution time required for αG-AA and L-ascorbic acid from anion exchange resins tends to longer and the concentration of the resulting αG-AA tends to lower.

After being purified and concentrated into supersaturated solutions, fractions rich in αG-AA, which had been desorbed and eluted from anion exchange resins packed in columns, can be facilitated to form αG-AA crystals and to yield a high αG-AA content product in a crystalline form. Fractions rich in L-ascorbic acid can be reused as a material for the next enzymatic reaction to form αG-AA. Reuse of mixture fractions of incompletely separated αG-AA and L-ascorbic acid, as a material solution in the present invention, advantageously facilitates to yield high αG-AA content products and high L-ascorbic acid content products in a relatively-high yield.

The process for producing α-G-AA of the present invention has satisfactory advantages in processibility and production cost and makes it possible to produce high αG-AA content products with satisfactory high-quality and a purity of at least about 90%, d.s.b., in a yield of αG-AA of at least 85%, preferably, at least 90% to the αG-AA in the material solutions.

The high αG-AA content products thus obtained are stable high L-ascorbic acid content products which can be arbitrarily used as a vitamin C-enriching agent, stabilizer, quality improver, antioxidant, physiologically-active substance, and ultraviolet absorbent in a wide variety of fields of food products, cosmetics, pharmaceuticals, feeds, pet foods, industrial materials, etc.

The following experiment describes the present invention in detail:

Experiment

Figure 3:
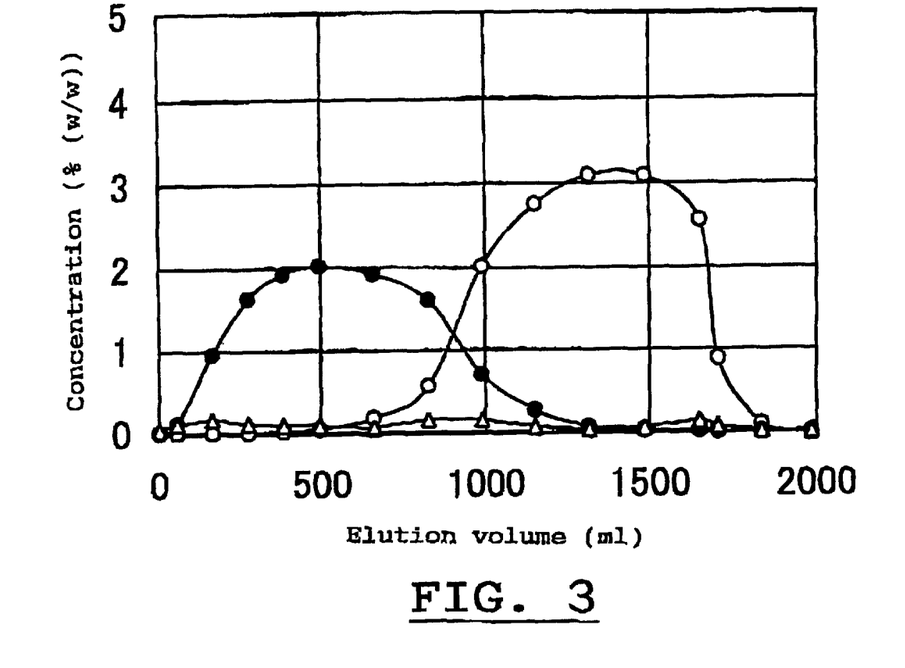
FIG. 3 is an elution curve for concentration distribution drawn by plotting solid concentrations for each component of αG-AA or L-ascorbic acid eluted from a column packed with "AMBERLITE IRA411S (OH-form)", an anion exchange resin commercialized by Rohm & Haas Co., USA, using 0.1 N aqueous hydrochloric acid solution as an eluent.
Figure 4:
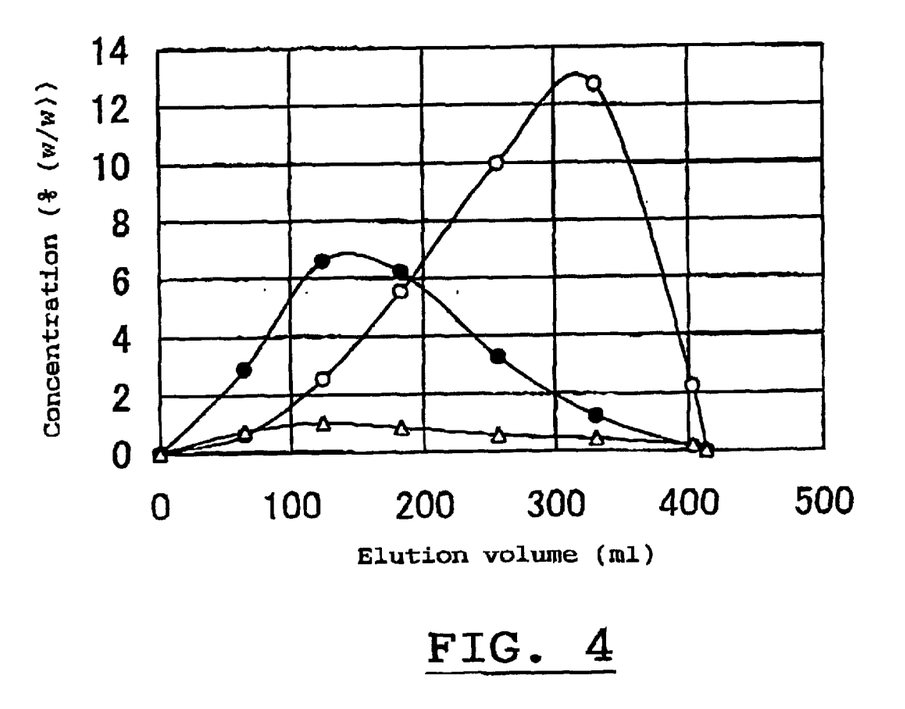
FIG. 4 is an elution curve for concentration distribution drawn by plotting solid concentrations for each component of αG-AA or L-ascorbic acid eluted from a column packed with "AMBERLITE IRA411S (OH-form)", an anion exchange resin commercialized by Rohm & Haas Co., USA, using 0.5 N aqueous hydrochloric acid solution as an eluent.

Influence of Concentration of Eluent on Separation and Elution of αG-AA and L-ascorbic Acid Adsorbed on Anion Exchange Resin Two parts by weight of dextrin (DE of about six) were dissolved by heating in six parts by weight of water, and under reducing conditions, the solution was admixed with one part by weight of L-ascorbic acid. The mixture Was kept at pH 5.5 and 60° C. and admixed with 400 units/g dextrin of cyclomaltodextrin glucanotransferase, commercialized by Hayashibara Biochemical Laboratories, Inc., Okayama, Japan, and enzymatically reacted for 24 hours. The reaction mixture was filtered with a UF membrane to remove the remaining enzyme, and the filtrate was adjusted to 55° C. and pH 5.0, admixed with 10 units/g dextrin of gluccamylase, commercialized by Seikagaku-Kogyo Co., Ltd., Tokyo, Japan, and enzymatically reacted for 24 hours. The resulting reaction mixture was heated to inactivate the remaining enzyme and decolored and filtered with an activate charcoal, followed by concentrating the resulting filtrate to give a concentration of about 40%. The solid composition of the concentrate was analyzed on high-performance liquid chromatography (HFLC) under the following conditions: "LC-6A" an HPLC apparatus commercialized by Shimadzu Corporation, Tokyo, Japan; "STP COLUMN ODS-II", a column commercialized by Shimadzu Techno Research Co., Tokyo, Japan; 0.02M $NaH_2PO_4$—$H_3PO_4$ (pH 2.0), an eluent; 0.5 ml/min, a flow rate; and "RI-8020", a differential refractometer commercialized by Tosho Corporation, Tokyo, Japan. As a result, the solid composition of the concentrate contained about 31% of αG-AA, about 21% of L-ascorbic acid, about 31% of D-glucose, and about 17% of α-glucosyl saccharide compounds. The above filtrate was demineralized by feeding at SV 2 to a column, having an inner diameter of 20 mm, a length of 350 mm, and an inner column temperature of 25° C. packed with 100 ml of "DIAION SK1B (H-form)", a strong-acid cation exchange resin commercialized by Mitsubishi Chemical Co., Tokyo, Japan, and kept at an inner column temperature of 25° C. Three hundred and thirty gram aliquots of the resulting eluate with a concentration of 30% were respectively fed at SV 2 to seven columns, each having an inner diameter of 20 mm, a length of 650 mm, and an inner column temperature of 25° C., packed with 200 ml of "AMBERLITE IRA411S (OH-form)", an anion exchanger commercialized by Rohm & Haas Co., Pennsylvania, U.S.A. Thereafter, about 1,000 ml water was fed at SV 2 to each column to wash the anion exchanger to elute non-adsorbed components from each column. To the seven columns were respectively fed, at SV 0.5, aqueous hydrochloric acid solutions of 0.1 N, 0.15 N, 0.2 N, 0.3 N, 0.4 N, 0.45 N and 0.5 N, and the fractionation of eluates was initiated after the solid concentration of the eluates eluted prom the outlets of each column reached to 0.2% or higher, and the fractionation was continued until each eluate was completely replaced with the aqueous hydrochloric acid solution of 0.1 N, 0.15 N, 0.2 N, 0.3 N, 0.4 N, 0.45 N or 0.5 N. Each fractionation was carried out by using a fraction collector at an interval of 20 min and sampled for analyzing the solid composition of each fraction on HPLC similarly as above. FIGS. 3 and 4 respectively show the elution curves for the concentration distributions, obtained based on the results by plotting the solid concentration of each component in each eluate when 0.1 N or 0.5 N aqueous hydrochloric acid solution was used as an eluent. In FIGS. 3 and 4, the axis of ordinates shows the solid concentration (% (w/w)), d.s.b., of each component, in each eluate; the axis of abscissas shows the elution volume (ml) from a column; and the symbols "-○-", "-●-", and "-Δ-" show αG-AA, L-ascorbic acid, and saccharides, respectively. From FIG. 3, αG-AA and L-ascorbic acid were satisfactorily separated under the conditions of using 0.1 N aqueous hydrochloric acid solution. However, comparing with the conditions of using a higher-concentration of aqueous solution of hydrochloric acid, the elution speed of αG-AA and L-ascorbic acid from a column tended to become low and the concentration of the resulting fractions rich in αG-AA and L-ascorbic acid tended to somehow become low. From FIG. 4, it was revealed that, under the conditions of using 0.5 N aqueous hydrochloric acid solution for desorption, comparing with the conditions of using aqueous solutions of hydrochloric acid with a relatively-low concentration, the elution speed of αG-AA and L-ascorbic acid from a column increases and results in an incomplete separation of αG-AA and L-ascorbic acid and in a reduction of the yield of high αG-AA content fraction. As evident from the results in FIGS. 3 and 4, it was revealed that most of the saccharides were not absorbed on the anion exchange resins but slightly adsorbed thereupon and eluted therefrom with eluents.

Although not concretely shown with figure, it was revealed that, under the conditions of using 0.1–0.45 N of aqueous hydrochloric acid solutions, αG-AA and L-ascorbic acid were satisfactorily separated and eluted from a column, particularly, their separation and elution were more effective under the conditions of using 0.2-0.3 N of aqueous hydrochloric acid solutions. The results, obtained from the conditions using aqueous hydrochloric acid solutions as an eluent, ate applicable to that in the case of using, as an eluate, aqueous solutions of other different kinds of acids, salts, or combinations thereof in place of the above aqueous hydrochloric acid solutions; and to that using other different types of anion exchange resins.

The following examples describe the process for producing high αG-AA content products of the present invention in more detail:

EXAMPLE 1

Figure 5:
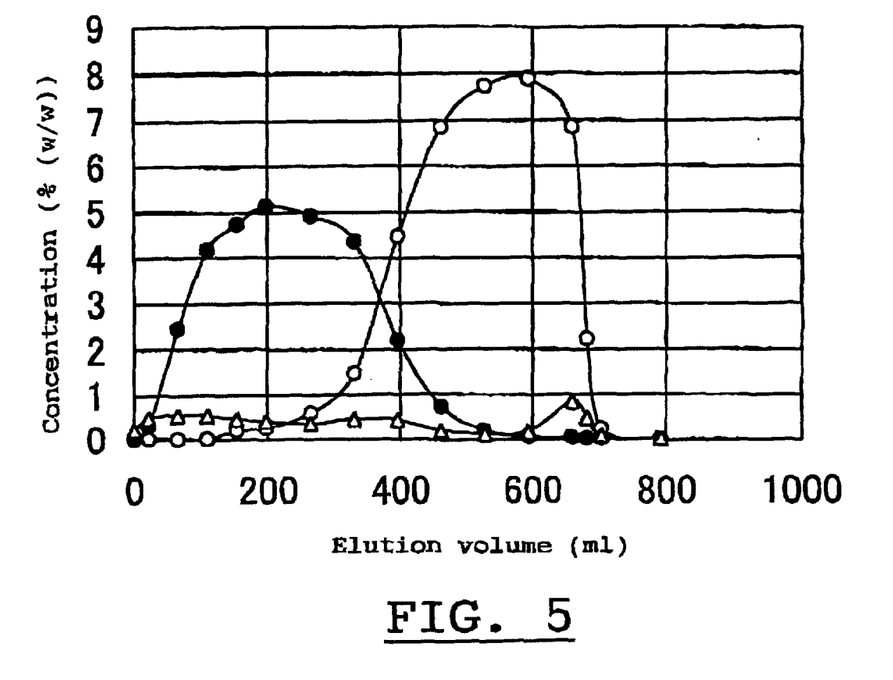
FIG. 5 is an elution curve for concentration distribution drawn by plotting solid concentrations for each component of αG-AA or L-ascorbic acid eluted from a column packed with "AMBERLITE IR-411S (OH-form)", an anion exchanger commercialized by Rohm & Haas Co., USA, using 0.25 N aqueous hydrochloric acid solution as an eluent.

Process for Producing High αG-AA Content Product

αG-AA High content product was obtained under the same conditions as used in the above experiment except for using a 0.25 N aqueous hydrochloric acid solution as an eluent. The eluate from the anion exchanger in this example was fractionated similarly as in the above experiment and sampled for analyzing the solid composition on HPLC. FIG. 5 is an elution curve that shows the concentration distribution drawn, based on the analysis data, by plotting the solid concentrations of each component in each eluate. In FIG. 5, the axis of ordinates shows the solid concentration (% (w/w)), d.s.b. of each component to the solid contents in each eluate; the axis of abscissas, elution volume (ml) from the column; the symbol "-○-", αG-AA; the symbol "-●-", L-ascorbic acid; and the symbol "-Δ-", saccharides. The high αG-AA content product, obtained in this example, contained αG-AA with a purity of about 93%, d.s.b., in a yield of about 92% to the content of αG-AA in the material solution. As evident from FIG. 5, it was revealed that most of the saccharides were not absorbed on the anion exchanger but slightly adsorbed thereupon and eluted therefrom with the eluent.

EXAMPLE 2

Process for Producing High αG-AA Content Product

Figure 6:
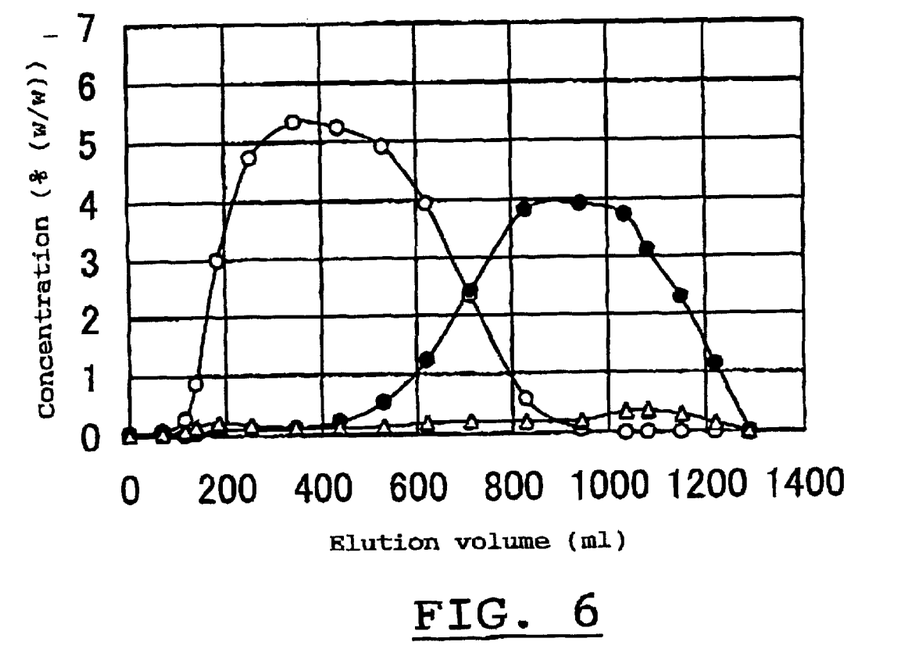
FIG. 6 is an elution curve for concentration distribution drawn by plotting solid concentrations for each component of αG-AA or L-ascorbic acid eluted from a column packed with "DIAION (OH-form)", an anion exchanger commercialized by Mitsubishi Chemical Co., Tokyo, Japan, using 0.25 N aqueous hydrochloric acid solution as an eluent.

Two parts by weights of dextrin (DE or about six) were dissolved by heating in six parts by weight of water, and under reducing conditions, the solution was then admixed with one part by weight of L-ascorbic acid and further admixed with 400 units/g dextrin of cyclomaltodextrin glucanotransferase, commercialized by Hayashibara Biochemical Laboratories, Inc., Okayama, Japan, and enzymatically reacted at pH 5.5 and 60° C. for 24 hours. The reaction mixture was filtered with a UF membrane to remove the enzyme, and the filtrate was adjusted to 55° C. and pH 5.0, admixed with 10 units/g dextrin of glucoamylase, commercialized by Seikagaku-Kogyo Co., Ltd., Tokyo, Japan, and subjected to an enzymatic reaction for 24 hours. The resulting reaction mixture was heated to inactivate the remaining enzyme, decolored, and filtered with an activated charcoal, and then the filtrate was concentrated to give a solid concentration of about 40%, The analysis of the solid composition of the concentrate under the same HPLC conditions as used in the above experiment revealed that the solid composition contained about 31% of αG-AA, about 21% of L-ascorbic acid, about 31% of D-glucose, and about 17% of α-glucosyl saccharide compound. While the above filtrate, which had been decolored and filtered with the activated charcoal, was demineralized by feeding at SV 2 to a column (20 mm in inner diameter, 350 mm in length, 25° C. of inner column temperature) packed with 100 ml of "DIAION SK1B (H-form)", a strong-acid cation exchanger commercialized by Mitsubishi Chemical Co., Tokyo, Japan. Three hundred and thirty grams of the resulting demineralized solution with a concentration of 30% was fed at SV 2 to a column (20 mm in inner diameter, 650 mm in length, 25° C. of inner column temperature) packed with 200 ml of "DIAION WA30 (OH-form)", an anion exchanger commercialized by Mitsubishi Chemical Co., Tokyo, Japan, and washed with 1,000 ml of water by feeding at SV 2 to desorb and elute non-adsorbed components from the exchanger. Thereafter, 0.25 N aqueous hydrochloric acid solution as an eluent was fed to the column at SV 0.5, and the collection of the eluate was initiated after the concentration of eluate, eluted from the outlet of the column, reached to a concentration of 0.2% or higher; and continued until the eluate was replaced with the aqueous 0.25 N hydrochloric acid solution. Using a fraction collector, the eluate was fractionated and sampled at an interval of 20 min, and the solid composition of each sample was analyzed on HPLC similarly as in the above experiment. FIG. 6 shows an elution curve for concentration distribution drawn by plotting the solid concentration of each component in each eluate. As evident from FIG. 6, the elution order of αG-AA and L-ascorbic acid was reversed to that of Example 1 because of the use of a different anion exchanger from that of Example 1, and the separation of αG-AA and L-ascorbic acid was satisfactory, similarly as in Example 1, yielding in a high αG-AA content product by collecting a desired fraction rich in αG-AA. In FIG. 6, the axis or ordinates shows the solid concentration (%(w/w)), of each component to the solid contents in each eluate; the axis of abscissas, elution volume (ml) from the column; the symbol "-○-", αG-AA; the symbol "-●-", L-ascorbic acid; and the symbol "-Δ-", saccharides. As evident from FIG. 6, αG-AA and L-ascorbic acid were satisfactorily desorbed and eluted from the anion exchanger, yielding in a high αG-AA content product by collecting a desired fraction rich in αG-AA. The product contained αG-AA with a purity of about 93%, d.s.b., and had a yield of about 90% to the content of αG-AA in the material solution. As evident from FIG. 6, it was revealed that most of the saccharides were not absorbed on the anion exchanger but slightly adsorbed thereupon and eluted therefrom with the eluent.

EXAMPLE 3

Process for Producing High αG-AA Content Product

A high αG-AA content product was produced under similar conditions as used in Example 2 except for using a column (400 mm in inner diameter, 1,000 mm in length) packed with "DIAION SK1B (H-form)", a strong-acid cation exchanger commercialized by Mitsubishi Chemical Co., Tokyo, Japan, for demineralization; a column (560 mm in inner diameter, 1,000 mm in length, 25° C. of inner column temperature), packed with "AMBERLITE IRA910CT (OH-form)", an anion exchanger commercialized by Rohm & Haas Co., Pennsylvania, U.S.A., as an anion exchanger; and 0.3 N aqueous nitric acid solution as an eluent. The high αG-AA content product had a liquid form, a purity of about 92%, and an αG-AA yield of about 90% to the content of αG-AA in the material solution. The liquid high αG-AA content product was concentrated in vacuo into a solution with a solid concentration of about 76%, placed in a crystallizer, admixed with one percent, d.s.b., of αG-AA crystal as a seed, kept at 40° C., and then moderately cooled to 25° C. over two days under gentle stirring conditions and separated by using a basket-type centrifuge. The resulting crystals were washed by spraying with a small amount of water, followed by collecting αG-AA in a crystalline form to obtain a high αG-AA content product with a purity of about 99%, d.s.b.

EXAMPLE 4

Process for Producing High αG-AA Content Product

A high αG-AA content product was produced under the similar conditions as used in Example 2 except for using 0.45 N aqueous hydrochloric acid solution as an eluent. Similarly as in Example 2, αG-AA and L-ascorbic acid were satisfactorily eluted from the anion exchanger packed in a column. The high αG-AA content product, obtained in this example, contained αG-AA with a purity of about 90%, d.s.b., and had an αG-AA yield of about 91% to the content of αG-AA in the material solution.

EXAMPLE 5

Process for Producing High αG-AA Content Product

A high αG-AA content product was produced under similar conditions as used in Example 2 except for using a column (800 mm in inner diameter, 1,600 mm in length) packed with "DIAION SK1B (H-form)", a strong-acid cation exchange resin commercialized by Mitsubishi Chemical Co., Tokyo, Japan, for demineralization; a column (1,200 mm in inner diameter, 1,600 mm in length, 25° C. of inner column temperature) packed with "AMBERLTTE IRA478RF (OH-form)", an anion exchanger commercialized by Rohm & Haas Co., Pennsylvania, U.S.A., as an anion exchanger; and 0.2 N aqueous sodium chloride solution as an eluent. The high αG-AA content product was a sodium salt form of cxGMA (αG-AA-Na), containing αG-AA-Na with a purity of about 90% and had an αG-AA-Na yield of about 90% by molar ratio to the content of αG-AA-Na in the material solution.

As described above, the present invention makes it possible to produce a high αG-AA content product and a high L-ascorbic acid content product in a relatively-high yield by a process comprising the steps of: contacting a solution, as a material solution, containing αG-AA, L-ascorbic acid, and a saccharide(s), with an anion exchange resin packed in a column, to adsorb the αG-AA and the L-ascorbic acid on the anion exchanger; washing the exchanger with water to remove the saccharide(s) therefrom; feeding to the column an aqueous solution, as an eluent, of an acid and/or a salt with a concentration of less than 0.5 N to fractionate a fraction rich in αG-AA and a fraction rich in L-ascorbic acid; and collecting the former fraction. According to the present invention, both a column chromatography using a strongacid cation exchanger, that is requisite for precolumn chromatography using an anion exchanger as used in conventional process for producing high αG-AA content products, and the concentration step requisite for a pretreatment for column chromatography using a cation exchanger can be omitted, and this simplifies the production process of αG-AA, lowers the production cost, and yields a high αG-AA content product in a relativelyhigh yield. Unlike conventional processes, the process of the present invention needs no column chromatography using a strong-acid cation exchange resin, and this makes it possible to increase the αG-AA yield from a level of about 75–80% as in conventional processes up to a level of about 85% or higher, preferably, 90% or higher to the αG-AA in a material solution.

Thus, the present invention provides a process for producing high αG-AA content products with a satisfactory processibility, production cost, yield, and quality. The high αG-AA content products can be arbitrarily used as a stable high L-ascorbic acid content product, vitamin C-enriching agent, stabilizer, quality improver, anti-oxidant, physiologically active substance, ultraviolet absorbent, etc., in a variety of fields of food products, cosmetics, pharmaceuticals, feeds, pet foods, industrial materials, etc.

The present invention with such an outstanding functions and effects will greatly contribute to this art.

We claim:

1. A process for producing 2-O-α-D-glucopyranosyl-L-ascorbic-acid, content product, which comprises the steps of:

contacting a solution containing 2-O-α-D-glucopyranosyl-L-ascorbic acid, L-ascorbic acid, and at least one saccharide, with an anion exchange resin packed in a column to adsorb said 2-O-α-D-glucopyranosyl-L-ascorbic acid and said L-ascorbic acid on said anion exchange resin;

washing said anion exchange resin with water to remove said saccharide(s) from said anion exchange resin;

feeding to said column an aqueous solution, as an eluent, of an acid and/or a salt with a concentration of less than 0.5 N to fractionate a fraction rich in 2-O-α-D-glucopyranosyl-L-ascorbic acid and a fraction rich in L-ascorbic acid; and collecting said fraction rich in 2-O-α-D-glucopyranosyl-L-ascorbic acid.

2. The process of claim 1, wherein said solution is obtained by allowing a saccharide-transferring enzyme with or without glucoamylase to act on a solution containing L-ascorbic acid and α-glucosyl saccharide compound.

3. The process of claim 1, wherein said solution is obtained by contacting with a cation exchange resin in an H-form to remove minerals.

4. The process of claim 1, wherein said anion exchange resin is an anion exchange resin in an OH-form.

5. The process of claim 1, wherein said acid is one or more members selected from the group consisting of hydrochloric acid, sulfuric acid, nitric acid, and citric acid.

6. The process of claim 1, wherein said salt is one or more members selected from the group consisting of sodium chloride, potassium chloride, sodium sulfate, sodium nitrate, potassium nitrate, sodium citrate, and potassium citrate.

7. The process of claim 1, wherein said aqueous solution of said acid and/or said salt has a concentration of 0.1–0.45 N.

8. The process of claim 7, wherein said aqueous solution of said acid and/or said salt has a concentration of 0.2–0.3 N.

9. The process of claim 1, which further contains the steps of concentration and crystallization.

* * * * *